(12) United States Patent
Schaumberg

(10) Patent No.: US 11,934,174 B2
(45) Date of Patent: Mar. 19, 2024

(54) METHOD AND SYSTEM FOR DETERMINING A TENSION VALUE OF A LIMB OF A PERSON AND COMPUTER PROGRAM

(71) Applicant: MEDI GMBH & CO. KG, Bayreuth (DE)

(72) Inventor: Maximilian Schaumberg, Bayreuth (DE)

(73) Assignee: MEDI GMBH & CO. KG, Bayreuth (DE)

( * ) Notice: Subject to any disclaimer, the term of this patent is extended or adjusted under 35 U.S.C. 154(b) by 1102 days.

(21) Appl. No.: 16/742,747

(22) Filed: Jan. 14, 2020

(65) Prior Publication Data

US 2020/0249657 A1    Aug. 6, 2020

(30) Foreign Application Priority Data

Feb. 5, 2019  (EP) .................................... 19155558

(51) Int. Cl.
*G05B 19/4155* (2006.01)
*A61B 5/00* (2006.01)
(Continued)

(52) U.S. Cl.
CPC ........ *G05B 19/4155* (2013.01); *A61B 5/0064* (2013.01); *A61F 13/00987* (2013.01);
(Continued)

(58) Field of Classification Search
CPC ...... G05B 19/4155; G05B 2219/45196; A61B 5/0064; A61B 5/442; A61B 2090/367;
(Continued)

(56) References Cited

U.S. PATENT DOCUMENTS

| 2010/0172567 A1* | 7/2010 | Prokoski | .............. | A61B 5/0064 |
|---|---|---|---|---|
| | | | | 348/47 |
| 2011/0016602 A1* | 1/2011 | Berns | ................. | A41D 13/0015 |
| | | | | 703/2 |

(Continued)

OTHER PUBLICATIONS

Krzysztof Kowalski et al, "Influence of a Compression Garment on Average and Local Changes in Unit Pressure", Fibres and Textiles in Eastern Europe, vol. 25, No. 0, Dec. 13, 2017, pp. 68-74, PL.

(Continued)

*Primary Examiner* — Matthew Kremer
*Assistant Examiner* — Jonathan Drew Moroneso
(74) *Attorney, Agent, or Firm* — Rimon PC

(57) ABSTRACT

Computer-implemented method for determining a tension value of a limb of a person, the tension value of the limb being used along with a skin value of the limb for production of a custom-tailored compression garment for the limb, the skin value describing the circumference of the limb without any applied compression and the tension value describing the circumference of the limb with the compression garment applying a desired compression, wherein the skin value of the limb is received and the tension value of the limb is calculated from the skin value according to a calculation instruction parametrized by at least one parameter, the parameter being derived from a dataset comprising multiple associated tuples of skin values and tension values.

14 Claims, 1 Drawing Sheet

Figure 1:
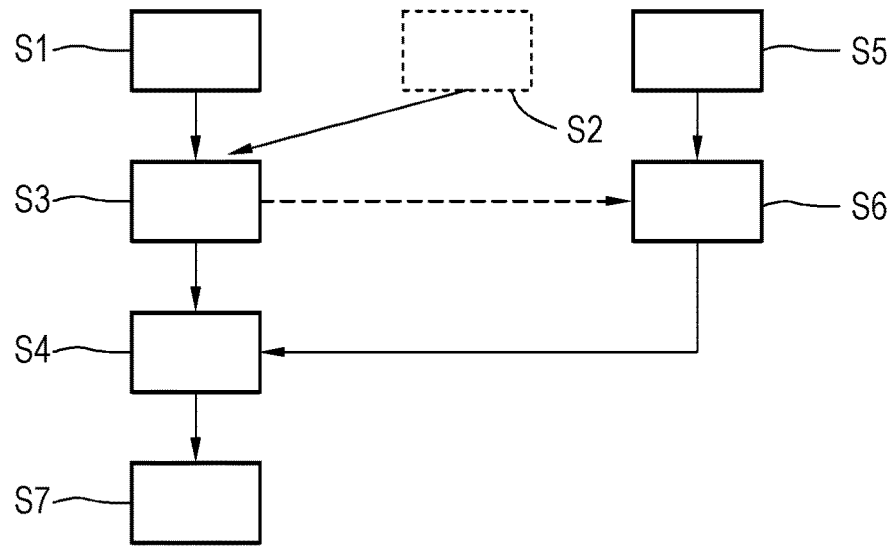

(51) Int. Cl.
  *A61F 13/00* (2006.01)
  *A61F 13/08* (2006.01)
  *D04B 1/26* (2006.01)
  *D04B 21/20* (2006.01)
  *A61B 90/00* (2016.01)

(52) U.S. Cl.
  CPC ............... *A61F 13/08* (2013.01); *D04B 1/26* (2013.01); *D04B 21/207* (2013.01); *A61B 5/442* (2013.01); *A61B 2090/367* (2016.02); *D10B 2509/028* (2013.01); *G05B 2219/45196* (2013.01)

(58) Field of Classification Search
  CPC ... A61B 5/1072; A61B 5/1079; A61B 5/6898; A61B 5/7264; A61B 5/0022; A61F 13/00987; A61F 13/08; D04B 1/26; D04B 21/207; D04B 9/52; D04B 37/02; D10B 2509/028; G16H 50/50; G16H 20/30; G16H 50/70
  See application file for complete search history.

(56) References Cited

U.S. PATENT DOCUMENTS

2017/0281009 A1* 10/2017 Obropta, Jr. ........... A61B 5/442
2018/0168261 A1 6/2018 Weiler et al.

OTHER PUBLICATIONS

Rong Liu et al, "Determination of leg cross-sectional curvatures and application in pressure prediction for lower body compression garments", Textile Research Journal, vol. 89, No. 10, Jun. 11, 2018, pp. 1835-1852, GB.

* cited by examiner

METHOD AND SYSTEM FOR DETERMINING A TENSION VALUE OF A LIMB OF A PERSON AND COMPUTER PROGRAM

CROSS-REFERENCE TO RELATED APPLICATIONS

This application claims priority to European Patent Application serial number 19155558.0, filed Feb. 5, 2019, the contents of each of which are incorporated herein by reference in their entirety.

The invention concerns a computer-implemented method and a determination system for determining a tension value of a limb of a person, the tension value of the limb being used along with a skin value of the limb for production of a custom tailored compression garment for the limb, the skin value describing the circumference of the limb without any applied compression and the tension value describing the circumference of the limb with the compression garment applying a desired compression. The invention further concerns a method for producing a compression garment for a limb of a person and a computer program.

Compression garments have already been proposed in the state of the art and exist in a wide variety of embodiments and for various applications. Compression garments are used to apply a desired compression to a limb of a garment, in particular for therapeutic reasons. Known compression garments comprise compression wraps, compression stockings, compression bandages and the like. As the properties of the limbs of persons usually differ from each other, to achieve the desired therapeutic effect, it is known to produce these compression garments custom-tailored for a certain person, for example a patient. In particular, measurements may be performed at the limb of the patient to obtain measurement values, which can be used for production of a customized compression garment for the person.

In known approaches, at different measurement positions along the limb, a so-called skin value (or "skin measure") and so-called tension value (or "tension measure"/"tight tape measure"), which, in German, are called "Hautmaß" and "Zugmaß", are measured, for example by staff of a medical store. The measurement positions may be defined by a standard, for example RAL-GZ 387/1. Measurement using tension and/or no tension is, for example, described in Anett Reißhauer et al., "Kompendium der lymphologischen Kompressionsversorgung", Bundesfachschule für Orthopädie-Technik, ISBN: 978-3-00-024717-0. The skin value is the circumference of the limb at the skin surface without applying pressure onto the human tissue. The tension value, however, is determined under tension of the measuring tape, where it is, the measuring tape is pulled tight and applies pressure onto the tissue which should at least essentially resemble the compression to be applied by the compression garment. That is, the tension value is heavily dependent on the skill level, sensitivity and experience of the person performing the measurement. While the skin value may, for example, also be determined by other means, for example imaging or scanning devices, the tension value can, to date, only be determined by manual measurement using a certain tension, such that the quality and reliability of the tension value rests in the hands of the staff of medical stores.

However, the tension value is a very important information for producing a fitting custom-tailored compression garment of a high quality, since, for example, knitting parameters for automatic knitting machine are determined depending on the skin value as well as the tension value. An additionally known measurement value is, for example, the table value (or "table measure"), that is, the circumference of the compression garment while not donned.

In summary, to obtain the tension value, a certain tension/force is applied by the person performing the measurement. This applied tension is only based on know-how/experience of the person performing the measurement. In consequence, faulty measurements are common such that the persons for whom garments are produced often file complaints. Additionally, staff of medical stores is often overchallenged.

It is thus an object of the current invention to provide a possibility to simplify the measurement process regarding custom-tailored garments and/or to standardize the measurement results regarding tension values.

This object is achieved by providing the methods, determination system and computer program according to the independent claims. Advantageous embodiments are described in the dependent claims.

In a computer-implemented method as initially described, according to the invention, the skin value of the limb is received and the tension value of the limb is calculated from the skin value according to a calculation instruction parametrized by at least one parameter, the parameter being derived from a dataset comprising multiple associated tuples of skin values and tension values.

By analyzing data on skin value and tension value, the inventors have surprisingly discovered that there is a correlation between skin value and tension value suitable for calculating the tension value from the skin value. This allows only performing the (well-defined) measurement regarding the skin value, for example manually or by using an imaging or scanning device, as will be further elaborated below. The method according to the invention receives the skin value and uses the calculation instruction to calculate the tension value from the skin value. The calculation instruction is parametrized by at least one parameter, which may be determined by evaluating known data on skin measurements and associated tension values. The calculation instruction thus describes the correlation between the skin value and the tension value, for example according to a mathematical function whose coefficients, that is, the at least one parameter, is determined in a fitting process.

In this context, the higher the number of data points, that is, tuples, in the dataset, the better can the correlation between skin value and tension value be described. In this respect, it is particularly advantageous to use so-called big data evaluation to determine the parameter. In concrete embodiments, the dataset may comprise at least 1,000 different tuples, in particular at least 100,000 different tuples.

By using a calculation instruction to calculate the tension value of the limb from the skin value of the limb, a standardized, consistent, unified and reproducible method for determining the tension value is provided. Since, preferably, the tuples in the dataset relate to actually produced compression garments, a reliable foundation is provided and realistic correlations are derived.

In most cases, the skin value and the tension value will be required at different measurement positions along the length of the limb. That is, generally, at least one measurement position, in particular in form of a length value, will be associated with each pair of skin value and tension value. In particular, these measurement positions may be defined by an standard. In German, the measurement position associated with the other values may also be called "Längsmaß".

In a preferred, simply realizable embodiment, the parameter may be a factor with which the skin value of the limb is multiplied. Of course, the factor may also be used to perform a division. In this manner, a simple calculation instruction is provided, in particular as tension value=factor*skin value. Other or extended calculation instructions, for example comprising addition or subtraction, are also conceivable.

In an especially preferred embodiment, at least one input classification information, each relating to an information class, is provided along with the skin value of the limb, wherein the at least one parameter is chosen depending on the input classification information and/or as a parameter associated with the input classification information. The input classification information allows a refinement regarding the correlations, since the concrete parameters may also depend on such additional information, for example gender, such that, in this example, different parameters apply for male and female persons. To derive parameter values for different classification information relating to an information class, preferably each tuple of the dataset additionally comprises, for each information class, a dataset classification information associated with its skin value and tension value, wherein the parameter is determined from at least one subset of the dataset tuples comprising at least one dataset classification information matching the corresponding input classification information and/or by interpolation regarding at least one of the at least one input classification information. That is, the dataset can be organized into subsets relating to certain classification information of certain information classes. In the above-mentioned example of the gender of the person, for example, there may be a subset containing tuples for male persons and a subset containing tuples for female persons. However, usually, multiple information classes will be used, such that subdivisions for each information class and/or subdivisions regarding groups of information classes may be performed, yielding, for example, subsets regarding females of one age group and another subset regarding males of another age group and so on.

In particular, regarding the use of multiple information classes, different approaches may be taken to derive parameters depending on the correspondingly provided input classification information, which can also be used complementary.

In a first approach, subparameters may be determined for at least two subsets relating to different information classes, wherein the parameter is determined by using an, in particular weighted, mean of the subparameters. In this embodiment, subsets for groups of information classes and/or, preferably, single information classes, are defined to form subsets dividing the whole dataset according to different classification information of the respective information class or information classes. For example, regarding the gender of the person, the dataset may be subdivided into the first subset regarding male persons and a second subset regarding female persons. The same can be done for other single information classes or groups of information classes. For example, if a second information class concerns the age of the person, subsets for different age categories, that is, intervals of the age as classification information, may be formed. If, now, the input classification information relates to a person of certain gender and certain age category, subparameters may be derived from the subsets relating to the same input classification information. A parameter may be determined by taking the mean of the two subparameters, or, preferably, the weighted mean, such that, for example, gender has a higher weight than age or vice versa. Generally, more than two subparameters may be determined and, in particular, respectively weighted. This approach thus adds a lot of flexibility regarding the influence of certain input classification information. In particular, the weights themselves may be determined from the dataset, in particular by evaluating the differences of subparameters derived from the subsets for different values of the classification information for each information class.

In another embodiment, which may also be used in combination with the first embodiment, the parameter or at least one subparameter may be determined from a subset for which at least two input classification informations match the corresponding dataset classification information. In this approach, the intersections between subsets regarding a single information class are determined as the relevant subset, from which the parameter or at least one subparameter is determined. For example, if a gender of the person is used as an information class and the age group is used as another information class, the relevant subset may only contain the persons of the gender and age group provided as input classification information. This may lead to a higher quality approximation of the parameter, but requires larger numbers of tuples.

In concrete embodiments, the at least one information class may be chosen from a group comprising a country class describing a country where the compression garment is to be used, a compression class, a garment information class, an indication class containing medical indications to be treated using the compression garment, a measurement position class comprising measurement positions along the length of the limbs, a limb class, a person age class, a person weight class, a person gender class, a compression garment length class, and a person tissue property class.

It can be shown that, in different countries, different requirements or desires regarding the wearing comfort of the compression garment exist, such that a country class may be used as an information class. For example, when evaluating the dataset, different parameters may result for different countries.

Compression classes of compression garments are already known in the state of the art and provide information regarding the desired compression to be applied to the limb. This, in turn, may lead to different tension values to achieve the desired compression level. For example, mild compression may relate to compression values in the interval of 18 to 21 mmHg, moderate compression may be associated with the compression interval of 23 to 32 mmHg, and so on.

Regarding the possible garment information class, garment classification information may, for example, describe the type of the compression garment, and/or concrete properties, in particular an elasticity along at least one knitting direction and/or a wall stability of the compression garment. These compression garment properties may also influence the determination of tension values from skin values.

An indication class containing medical indications to be treated using the compression garment may describe what the aim of the treatment using the compression garment is, providing certain hints on the desired compression and/or other properties of the compression garment.

Regarding the measurement position class, measurement position classification information items may preferably be defined according to at least one standard, for example RAL-GZ 387/1 relating to compression stockings. For example, in case of a leg, certain predefined positions along the leg may be used to determine skin values and tension values for each of these positions to be able to produce a suitable compression garment, for example compression stocking.

In a limb class, limb classification information items may, for example, comprise a leg, an arm, or even finer distinctions, for example lower leg, upper leg, knee, foot and the like. In a patient age class, patient age classification information may be a certain age or a certain age group/category. The same may be true for a person weight class, while a person gender class, as already explained above, usually has only two classification information items, namely (biologically) male and female.

Regarding the compression garment length class, a compression garment length classification information may describe the at least one measurement position where the garment ends, such that different compression properties/different desired compressions may be associated with this measurement position along the length of the limb, depending on whether the garment ends there or not. Usually, a compression garment provides less compression at the end positions. For example, compression stockings having different lengths are known in the state of the art, as well as compression wraps and/or compression bandages. It is, for example, possible, that a compression stocking ends at the knee or that it extends further to the upper legs.

Regarding the patient tissue property class, certain tissue properties may be described which may influence the tension value at the desired compression. Preferably, the tissue properties may be measured, that is, an input classification information of the patient tissue property class may be determined by measurement. For example, hardness testers or the like may be used.

It should be noted that it is also possible to provide at least one additional parametrizing information which is used as or for determination of at least one of the at least one parameter. In particular in cases, in which a relationship of the parameter to the additional parametrizing information is known theoretically and/or from other sources, in may be directly applied.

Each tuple of the dataset additionally comprises a reliability information associated with its skin value and tension value, wherein, when deriving the parameter from the dataset, tuples are excluded and/or weighted according to their reliability information. In particularly advantageous embodiments, the reliability information comprises information regarding complaints received relating to a compression garment produced using the skin value and the tension value of the tuple. In this manner, tuples relating to actually produced garments in which there has been a complaint, in particular regarding the fitting, may be excluded from deriving the parameter or at least lowly weighted, since the combination of skin value and tension value did not lead to satisfaction or contentment of the person for which the garment was produced. In this manner, suboptimally measured or even erroneous measurements may be excluded or have their impact reduced. Of course, also other reliability information may be used, for example, a confidence level entered by a person making measurements and/or an automatically deduced confidence information, for example depending on a known skill level/experience of a person taking the measurement underlying the tuple. If, as is preferred, the dataset is augmented by tuples being determined according to the current invention, a reliability information may also be determined based on the derivation of the parameter and/or the calculation of the tension value of the limb from the skin value of the limb. Known techniques and mathematical methods may be used to trace/keep track of possible errors, for example, the calculation of the standard deviation when determining the parameter from a dataset or at least one subset.

As already noted, preferably, new tuples, wherein the tension value has been calculated according to the invention, may preferably be added to the dataset. In an especially preferred embodiment, however, the skin value and the tension value of the limb are added as new tuples to the database only as soon as reliability information regarding these values becomes available. For example, if a compression garment is produced for the person, the corresponding tuple of skin value and tension value is not added to the dataset before feedback from the person for whom the compression garment has been produced if received. In this manner, the reliability information, in particular regarding the fitting of the compression garment, is already available when the new entry to the dataset is added and/or the addition of the tuple may be omitted if the reliability information indicates a low quality.

Preferably, the skin value is determined, in particular contact-free, using a 3D-scan device scanning the limb. In the state of the art, such 3D scanning devices for measuring a person or parts of a person, in this case the limb, in particular in a high precision, has already been proposed. Such 3D scan devices may in an advantageous way also be used in combination with the inventive method for determining the tension value. In particular, if a contact-free 3D scan device, for example an imaging-based device, is used, the whole procedure of measuring the limb becomes contact-free. In this case, no tension or force needs to be exerted onto the skin of the person. In summary, a highly comfortable and reliable way of measuring the information values required for producing the compression garment is provided, in particular opposed to the traditional, unreliable way of measuring the limb using a measuring tape.

In particular, a tablet or mobile phone running a scanning application computer program may be used as the 3D scan device. Tablets or mobile phones usually comprise an optical imaging sensor, in particular a camera, and/or position and/or acceleration sensors, the latter on particular allowing to derive a position information associated with images taken by the camera. Application computer programs ("apps") have been developed which evaluate images of a limb taken from different positions, in particular orientations with respect to the limb, such that the contour of the limb and thus the skin value may be determined. In such an advantageous embodiment of the current invention, staff at a medical store only needs a tablet or mobile phone to determine all information values relevant for producing a compression garment, in particular the skin value and the tension value, which is calculated from the skin value. No contact to the limb is required.

It should be noted at this point that a 3D scan device, in particular the application computer program, may also be configured to calculate the tension value itself, or, preferably, to send the measured skin value to another computing device, in particular of a determination system, where the tension value can be calculated. In particular, the computing device of the determination system may be or comprise at least one server of a manufacturer of compression garments, where also the dataset may be stored and/or the compression garment for the limb is automatically produced according to the received skin value and the calculated tension value, in particular also using at least part of the classification information provided. The 3D scan device may then use the internet to send the measured skin value and further information.

In this context, the invention also concerns a method for producing a compression garment for a limb of a person, comprising automatically performing the steps of a method for determining a tension value as described above, whereafter the compression garment is automatically produced by a garment production apparatus, in particular a knitting machine, using the received skin value and the determined tension value. In particular, a computing device of a manufacturer may thus receive, in particular along with input classification information, the skin value, for example measured in a medical store, of a limb of a person. Automatically, in particular also using input classification information, the tension value is calculated from the skin value. At this time, all information for automatically producing the custom-tailored compression garment for the limb of the person is available at the computing device of the manufacturer, such that the garment production apparatus, in particular a knitting machine, can be controlled to correspondingly produce the custom-tailored compression garment for the limb of the person. Thus, a fully automatic, reliable and simply implementable way of producing custom-tailored compression garments is provided.

As already noted, different types of compression garments may be produced according to the invention, for example compression stockings, compression bandages and/or compression wraps.

The invention also concerns a determination system for a tension value of a limb of a person, the tension value being used along with a skin value of the limb for production of a custom-tailored compression garment of the limb, the skin value describing the circumference of the limb without any applied compression and the tension value describing the circumference of the limb with the compression garment applying a desired compression, which is characterized by
an interface for receiving the skin value of the limb, and
a processor for calculating the tension value of the limb from the skin value according to a calculation instruction parametrized by at least one parameter, the parameter being derived from a dataset stored in a storage means of the determination system and comprising multiple associated tuples of skin values and tension values.

In other words, the determination system is configured to perform a method according to the current invention. All features and comments regarding the method according to the invention correspondingly apply to the determination system according to the invention.

The determination system may comprise one or more computing devices, in particular being or comprising at least one server. For example, a skin value measured in a medical store may be communicated, using the internet or another communication connection, to the interface, which is a part of at least one of the at least one computing device, in particular of a server. Here, the calculation of the tension value may take place. The dataset may be stored in the same computing device, in particular server. It is, however, also possible that the dataset is stored in the storage means of another computing device, in particular server. In preferred embodiments, if a tablet and/or a mobile phone, as discussed above, acts as 3D scanning device for measuring the skin value, the corresponding computer application program/the tablet or mobile phone may already be configured to send the measured skin value of the limb to the at least one computing device of the determination system, in particular the interface. It is, however, also possible to calculate the tension value in the tablet or mobile phone. In any case, the tablet or mobile phone may form part of the determination system.

In embodiments, a determination system may be part of a compression garment production system, which additionally comprises a garment production apparatus and an associated controller, wherein the controller controls the garment production apparatus to produce a compression garment using the received skin value and the determined tension value. To this end, a knitting program may be determined in the determinations system, for example in a computing device and/or using the controller.

It is noted that a processor according to the current invention is to be understood as any device that is able to process data. For example, the processor may be or comprise at least one CPU and/or GPU and/or integrated circuit and/or FPGA or the like. By the processor, certain functional units may be realized, for example a calculation unit for calculating the tension value of the limb from the received skin value of the limb.

A computer program according to the invention can, for example, be directly loaded into a storage means of a computing device, in particular the determination system, and comprises program means to perform the steps of a method according to the invention when the program is executed in the computing device. The computer program may be stored on an electronically readable storage medium, which thus comprises electronically readable control information stored thereon, which in turn comprises at least the computer program according to the invention and is configured such that, when the storage medium is used in a computing device, in particular a determination system, the steps of a method according to the invention are performed. The electronically readable storage medium may be a non-transitional storage medium, for example a CD-ROM.

Figure 2:
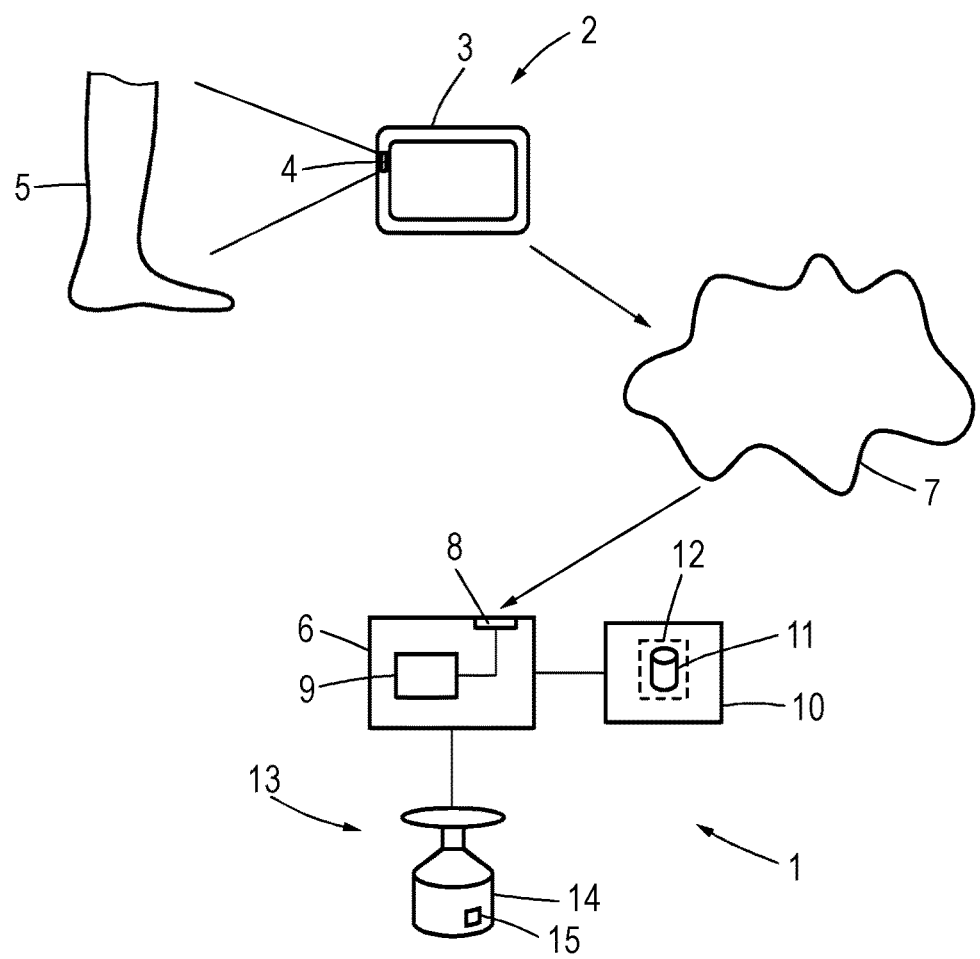

Further details and advantages of the current invention may be taken from the following description of preferred embodiments taken in conjunction with the drawings, in which:

FIG. 1 is a flowchart of an embodiment of a method according to the invention, and FIG. 2 shows an embodiment of a determination system according to the invention.

The flowchart of FIG. 1 illustrates an embodiment of a method according to the invention. The aim of the method described in the following is to produce a custom-tailored compression garment for the limb of a person. In a step S1, the skin value of the limb is measured, for example by staff of a medical store. The skin value of the limb may be taken manually at multiple measurement positions along the length of the limb which are relevant for the compression garment to be produced. The skin value is defined as the circumference of the limb at the measurement position with no tension or force exerted onto the skin.

Preferably, in step S1, the skin value may be measured using a 3D scan device, which may in particular be realized as a tablet or mobile phone on which an application computer program is provided. For example, a camera of the tablet or mobile phone may be used to image the limb from multiple views, which may be evaluated to derive the skin value. Alternatively to such a tablet or mobile phone, the 3D scan device may be a dedicated scanner, for example a whole-body scanner and/or a limb scanner. The use of a 3D scan device is advantageous, since a contact-free measurement is possible and the measurement is not confined to only a few measurement positions.

In a generally optional step S2, additional information regarding the person, in particular a patient, and/or the garment is gathered as input classification information for, in this case, multiple information classes. The information classes may comprise a country class describing a country where the compression garment is to be used, a compression class, a garment information class, an indication class containing medical indications to be treated using the compression garment, a measurement position class comprising measurement positions along the length of the limb, a limb class, a person age class, a person weight class, a person gender class, a compression garment length class and/or a person tissue property class. For example, input classification information may be entered using the 3D scan device, in particular the tablet or mobile phone. In the case of patient tissue properties, these may also be measured, for example by using a hardness tester or the like.

The measured skin values for each measurement position as well as the input classification information are transferred to a computing device, in particular a server, of a manufacturer of compression garments, where they are received in step S3. For example, the skin value of the limb and the additional classification information may, for example, be communicated using the internet.

In a step S4, a calculation instruction is used to calculate a tension value of the limb from the skin value of the limb using a calculation instruction, in this case by multiplying the skin value with a factor. The factor is thus a parameter of the calculation instruction. Since, in this embodiment, the parameter is determined depending on input classification information, in step S3, the input classification information has already been transferred to a parameter determination unit of the receiving computing device and/or an additional computing device.

In a storage means, a dataset comprising tuples of skin values and associated tension values, as well as dataset classification information associated with the pair of skin value and tension value, is stored. The maintenance of this dataset is indicated by a step S5 and takes place continuously.

In particular, all tuples present in the dataset relate to actually produced compression garments, such that a reliability information is also associated with each tuple. In this embodiment, the reliability information at least describes whether there has been a complaint regarding the fitting of the compression garment. New tuples, in this respect, as only added to the dataset once the respective reliability information becomes available. In particular, feedback regarding produced compression garments is awaited before a tuple is eligible for entry into the dataset.

In a step S6, a parameter to be used in step S4 is derived from the dataset also using the input classification information. Two examples for the case of multiple information classes used shall be discussed as examples here.

In a first concrete example, for each information class, subsets are derived from the dataset, wherein a subset for each information class is generated by selecting all tuples in which the input classification information of the information class equals the dataset classification information of the respective tuple. For example, if the information class is a person gender class, and the input classification information is "female", a respective subset contains all tuples that relate to female persons.

For each subset generated in this manner, a subparameter is derived, for example, by fitting the calculation instruction to the tuples in the subset. In this process, tuples for which the reliability information shows a complaint regarding fitting may be excluded or lower weighted.

From the subparameters for all information classes, the parameter is derived by calculating the mean, in particular a weighted mean, such that the impact of certain information classes may be taken into account.

In a second example, only one subset is generated from the dataset, the subset containing all tuples for which all input classification information match the respective dataset classification information. The subset is thus an intersection of all the subsets generated in the first example. From this subset, the parameter is, again, derived by fitting the calculation instruction to the tuples.

It should be noted that is of course also possible to combine the first example and the second example, for example by forming subsets for groups of information classes instead of only single classes. If a classification information includes a continuous value, it is also possible to derive, in particular by interpolation, a function which describes how the parameter depends on the respective classification information. For the respective information class, the parameter or subparameter may thus be calculated.

The parameter derived from the dataset depending on the input classification information in step S6 is then used in step S4 to calculate the tension value.

In a step S7, the measured skin value of the limb, the calculated tension value of the limb and the input classification information, at least in part, are used to produce a custom-tailored compression garment for a person. As has already been noted, feedback regarding the fitting may be awaited before entering the newly calculated tuple into the dataset.

FIG. 2 illustrates an exemplary determination system 1 for performing the method according to FIG. 1. In this case, the determination system 1 also comprises the 3D scan device 2, in particular a tablet 3, whose camera 4 may be used to accordingly scan the limb 5 of a person. The tablet 3 may also be used to gather and assemble the input classification information. It is noted at this point that the input classification information may, in particular, also be used to determine measurement positions at which the skin value is to be determined.

The measured skin values at the respective measurement positions and the input classification information are sent to a computing device 6 of the manufacturer of compression garments through the internet 7 and/or mobile networks. The skin values of the limb 5 and the input classification information are received by an interface 8. The computing device 6, which may be a server, in this case also comprises at least one processor 9 for performing the calculations in step S4 and S6. It is noted that the processor 9 may, at least in part, also be realized distributedly, for example regarding other computing devices 10 of the manufacturer, in particular other servers. In this example, the dataset 11 is stored in a storage means 12 of a second computing device 10. The store means 12 and thus the dataset 11 may be accessed by the processor 9.

The measured skin values, the corresponding calculated tension values (for each measurement position) and the input classification information are then transferred to a garment production apparatus 13, in this case a knitting machine 14, where they are used by a controller 15 to produce the custom-tailored compression garment for the limb 5 of the person. Alternatively, a knitting program may be compiled on a computing device 6, 10, according to these informations, and be transferred to the garment production apparatus 13.

It is noted that in some embodiments, the determination system may only comprise the at least one computing device 6, 10. If the garment production apparatus is added, the determination system 1 may also be understood as garment production system.

The invention claimed is:

1. A method for producing a compression garment for a limb of a patient, comprising:
   receiving a skin value of the limb;
   calculating a tension value of the limb from the skin value according to a calculation instruction parametrized by at least one parameter, the parameter being derived by evaluating known data on skin measurements and associated tension values from a dataset comprising multiple associated tuples of skin values and tension values of actually produced compression garments; and
   automatically producing a custom-tailored compression garment using a garment production apparatus, the skin value, and the tension value of the limb;
   wherein the tension value of the limb of the patient is automatically calculated, and
   wherein the skin values in the dataset describe a circumference of at least one limb without any applied compression and the tension values in the dataset describe the circumference of the at least one limb with pressure applying a desired compression.

2. The method according to claim 1, characterized in that the dataset comprises at least 1000 different tuples and the tuples describing the actually produced compression garments.

3. The method according to claim 1, characterized in that the parameter is a factor with which the skin value of the limb is multiplied.

4. The method according to claim 1, characterized in that at least one input classification information, each relating to an information class, is provided along with the skin value of the limb, wherein the at least one parameter is determined depending on the input classification information.

5. The method according to claim 4, characterized in that each tuple of the dataset additionally comprises, for each information class, a dataset classification information associated with its skin value and tension value, wherein the at least one parameter is determined from at least one subset of the dataset tuples comprising at least one different dataset classification information matching the corresponding input classification information and/or by interpolation regarding at least one of the at least one input classification information.

6. The method according to claim 5, characterized in that subparameters are determined for at least two subsets relating to different information classes, wherein the at least one parameter is determined by using a weighted mean of the subparameters, and/or that the parameter or at least one subparameter is determined from a subset for which at least two input classification information match the corresponding dataset classification information.

7. The method according to claim 4, characterized in that at least one information class is chosen from a group consisting of a country class describing a country where the compression garment is to be used, a compression class, a garment information class, an indication class containing medical indications to be treated using the compression garment, a measurement position class comprising measurement positions along a length of the limb, a limb class, a person age class, a person weight class, a person gender class, a compression garment length class, and a person tissue property class.

8. The method according to claim 7, characterized in that the input classification information of the patient tissue property class is determined by measurement.

9. The method according to claim 1, characterized in that each tuple of the dataset additionally comprises a reliability information associated with its skin value and tension value, wherein, when deriving the parameter from the dataset, tuples are excluded and/or weighted according to their reliability information.

10. The method according to claim 9, characterized in that the reliability information comprises information regarding complaints received relating to a compression garment produced using the skin value and the tension value of the tuple.

11. The method according to claim 1, wherein the skin value of the limb is determined by a contact-free method using a 3D scan device scanning the limb.

12. The method according to claim 11, characterized in that a tablet or mobile phone running a scanning application computer program is used as the 3D scan device.

13. The method according to claim 1, characterized in that the dataset comprises at least 100,000 different tuples, and the tuples describing the actually produced compression garments.

14. A compression garment production system, comprising:
   a garment production apparatus;
   an associated controller; and
   a determination system for a tension value of a limb of a person, the tension value of the limb being used along with a skin value of the limb for production of a custom-tailored compression garment for the limb, the skin value describing a circumference of the limb without any applied compression and the tension value describing the circumference of the limb with the compression garment applying a desired compression, the determination system comprising:
   an interface for receiving the skin value of the limb, and
   a processor for calculating the tension value of the limb from the skin value according to a calculation instruction parametrized by at least one parameter, the parameter being derived by evaluation known data on skin measurement and associated tension values from a dataset stored in a storage means of the determination system and comprising multiple associated tuples of skin values and tension values, the skin values in the dataset describe the circumferences of the limb without any applied compression and the tension values in the dataset describe the circumferences of the limb with pressure applying the desired compression;
   wherein the associated controller controls the garment production apparatus to produce the compression garment using the received skin value and the calculated tension value.

* * * * *